United States Patent
Shahar et al.

(10) Patent No.: US 11,713,285 B2
(45) Date of Patent: Aug. 1, 2023

(54) METHANATION AND RECOVERY METHOD, SYSTEM, AND APPARATUS

(71) Applicants: Shahar Golan Technology Soultions Ltd., Jerusalem (IL); Ariel Scientific Innovations Ltd., Ariel (IL)

(72) Inventors: Natan Shahar, Jerusalem (IL); Avshalom Davidesko, Ariel (IL); Ilia Ulitsin, Ariel (IL)

(73) Assignees: Shahar Golan Technology Soultions, Ltd., Jerusalem (IL); Ariel Scientific Innovations Ltd., Ariel (IL)

(*) Notice: Subject to any disclaimer, the term of this patent is extended or adjusted under 35 U.S.C. 154(b) by 0 days.

(21) Appl. No.: 17/528,587

(22) Filed: Nov. 17, 2021

(65) Prior Publication Data
US 2023/0150898 A1    May 18, 2023

(51) Int. Cl.
| | |
|---|---|
| C07C 1/12 | (2006.01) |
| B01J 19/24 | (2006.01) |
| C25B 1/04 | (2021.01) |
| C01B 32/50 | (2017.01) |

(52) U.S. Cl.
CPC ............... C07C 1/12 (2013.01); B01J 19/244 (2013.01); C01B 32/50 (2017.08); C25B 1/04 (2013.01); *B01J 2219/00076* (2013.01)

(58) Field of Classification Search
CPC .............. C07C 1/12; C25B 1/04; C01B 32/50
See application file for complete search history.

(56) References Cited

U.S. PATENT DOCUMENTS

| | | |
|---|---|---|
| 5,183,484 A | 2/1993 | Yamaguchi |
| 2005/0132884 A1 | 6/2005 | Xu et al. |
| 2007/0212295 A1* | 9/2007 | Woods ................ C01B 3/48 |
| | | 422/600 |
| 2009/0238742 A1 | 9/2009 | Liu et al. |
| 2012/0222426 A1 | 9/2012 | Macadam |
| 2013/0129584 A1* | 5/2013 | Park ................... B01J 37/0009 |
| | | 422/603 |
| 2013/0177481 A1 | 7/2013 | Hokari |
| 2013/0272939 A1 | 10/2013 | Liu et al. |
| 2017/0274317 A1 | 9/2017 | Bumb |
| 2020/0392053 A1 | 12/2020 | Winkler et al. |

(Continued)

FOREIGN PATENT DOCUMENTS

| | | |
|---|---|---|
| DE | 102012007136 | 10/2013 |
| DE | 102013110470 | 3/2015 |
| DE | 102013002021 | 6/2015 |

(Continued)

OTHER PUBLICATIONS

David W. Keith et al., A Process for Capturing CO2 from the Atmosphere, Joule 2, 1573-1594 (Aug. 15, 2018).

(Continued)

*Primary Examiner* — Jafar F Parsa
(74) *Attorney, Agent, or Firm* — David S. Taylor

(57) ABSTRACT

A method, a system, and an apparatus of certain embodiments are provided to recover water and carbon dioxide from combustion emissions. The recovery includes, among other things, electrolysis and carbon dioxide capture in a suitable solvent. The recovered water and carbon dioxide are subject to reaction, such as a catalytic methanation reaction, to generate at least methane.

20 Claims, 7 Drawing Sheets

(56) References Cited

U.S. PATENT DOCUMENTS

2021/0340078 A1    11/2021    Winkler et al.

FOREIGN PATENT DOCUMENTS

| DE | 102017204981 A1 | 9/2018 |
|----|----|----|
| EP | 1936128 | 6/2008 |
| EP | 2751307 | 7/2014 |
| JP | 2004261757 | 9/2004 |
| WO | WO2013029701 A1 | 3/2013 |
| WO | WO2013124632 A2 | 8/2013 |
| WO | WO2013190581 | 12/2013 |
| WO | WO2013190581 A1 | 12/2013 |
| WO | WO2015055349 A1 | 4/2015 |
| WO | WO2016115582 | 7/2016 |

OTHER PUBLICATIONS

A.P.H. Goede, CO2-Neutral Fuels, EPJ Web of Conferences 98, 07002, Dutch Institute for Fundamental Energy Research (2015).

Hsin-Ta Hsueh et al., Removal of CO2 from Flue Gas with Ammonia Solution in a Packed Tower, J. Environ. Eng. Manage., 20(1), 1-7 (2010).

Bryce Dutcher et al., Amine-Based CO2 Capture Technology Development from Beginning of 2013—A Review, ACS Applied Materials & Interfaces, 7, 2137-2148 (2015).

G. Granitsiotis, Methanation of Carbon Dioxide, Experimental Research of Separatioan Enhanced Methanation of CO2 (2017).

Hassan Ghanbarabadi et al., Simulation of CO2 Removal from Ethanwith Sulfinol-M+AMP Solvent . . . , Petroleum 5, 90-101 (2019).

Oliver Seyboth et al., Development of a Spray Scrubbing Process for Post Combustion CO2 Capture with Amine Based Solvents, Energy Procedia 63, 1667-1677 (2014).

Bingtao Zhao et al., Mass transfer performance of CO2 capture in rotating packed bed: Dimensionless modeling and intelligent prediction, Applied Energy 136, 132-142 (2014).

Zhiwu Liang et al., Review on current advances, future challenges . . . for post-combustion CO2 capture using amine-based absorbents, Chinese J. of Chem. Eng'g 24, 278-88 (2016).

Xiaomei Wu et al., Overall mass transfer coefficient of CO2 absorption in a diameter-varying spray tower, Energy Procedia 114, 1665-1670 (2017).

Hanna Karlsson et al., Rate of absorption of CO2 absorption systems using a wetted wall column Energy Procedia 114, 2009-2023 (2017).

Hongyi Dang, et al., CO2 absorption rate and solubility in monoethanolamine/piperazine/water, Separation Science and Tech., vol. 38, No. 2, 337-357 (2003).

Mohammad Heydarifard et al., Reactive absorption of CO2 into piperazine . . . modeling and experimental, Int'l J. of Greenhouse Gas Control 79, 91-116 (2018).

Jia-Lin Kang et al., Comparison between packed beds and rotating packed beds for CO2 capture using monoethanolamine . . . Int'l J. of Greenhouse Gas Control 46, 228-229 (2016).

M.R. Aliff Radzuan et al., Sustainable optimization of natural gas sweetening using a process simulation approach . . . , Materials Today: Proceedings 19, 1628-1637 (2019).

Chintana Saiwan et al., Part 3: Corrosion and prevention in post-combustion CO2 capture systems, Carbon Management, 2:6, 659-675 (2014).

International Search Report PCT/US2020/036063.
Written Opinion PCT/US2020/036063.
WO2016115582A, Jul. 28, 2016, machine translation.
Van der Zwet et al., Improved gas treating with sulfinol-x, Abstract (Sulfur (2010), 326, 53-57).
International Search Report and Notice of Transmittal for PCT/IB2022/000689 dated May 8, 2023, pp. 1-6.
PCT Written Opinion for PCT/IB2022/000689 dated May 8, 2023, pp. 1-9.

\* cited by examiner

METHANATION AND RECOVERY METHOD, SYSTEM, AND APPARATUS

BACKGROUND

Embodiments disclosed herein relate to methods, systems, and apparatuses for carrying out methanation and recovering and/or reclaiming methanation reactants from a combustion exhaust stream. Certain embodiments disclosed herein relate to methods, systems, and apparatuses for carrying out scrubbing, electrolysis, and thermal exchange operations in a common tank or chamber. Certain embodiments disclosed herein involve operations including carbon dioxide absorption and desorption. Certain exemplary embodiments involve the efficient use and transfer of heat between different operations.

Signatories to the Paris Climate Agreement are committed to steep reductions in greenhouse gas emissions, which include carbon dioxide, over the coming decade. The technological and economic challenge of meeting emission reductions under the Paris Climate Agreement is extremely significant. Fossil fuel-reliant industries such as power generation and manufacturing that output high levels of greenhouse gas emissions are especially vulnerable to new regulations that are rapidly reducing their profitability.

One solution for meeting the goals of the Paris Climate Agreement is renewable energy. Renewable energy is cheap and abundant when and where it is available. One of the problems with renewable energy sources is that the sources are not always available or plentiful. Unlike fossil fuels, which are dispatchable on demand to produce electricity or heat for satisfying consumer and business energy needs, photovoltaic (PV) solar power renewable energy is plentiful for typically less than 40% of the time, i.e., during peak sunlight hours. Wind turbines depend on environmental wind as a natural renewable energy resource; wind speeds can fluctuate greatly over the course of a day and adequate wind speeds are not abundant in many locales. Accordingly, the complete supplanting of non-renewable energy sources with renewable energy is, at the present time, likely infeasible given the world energy demands.

SUMMARY

This Summary is provided to introduce a selection of representative concepts in a simplified form, which representative concepts are further described below in the Detailed Description. This Summary is not intended to identify key features or essential features of the claimed subject matter, nor is it intended to be used to limit the scope of the claimed subject matter.

In an embodiment, a method includes receiving a hydrocarbon combustion exhaust stream including at least water and carbon dioxide in a chamber containing liquid water. The liquid water in the chamber, in an exemplary embodiment including water condensed from the exhaust stream, is subject to electrolysis to generate hydrogen and oxygen. Methanation reaction products are conveyed through one or more heat exchangers in the chamber to transfer heat from the methanation reaction products to the liquid water.

In another embodiment, a method includes subjecting liquid water in a chamber to electrolysis to generate hydrogen and oxygen, capturing carbon dioxide in a solvent, and conveying the solvent and the captured carbon dioxide through a first heat exchanger of the chamber. Methanation reaction products are conveyed through the a second heat exchanger, which may be the same as or different than the first heat exchanger, of the chamber to transfer heat from the methanation reaction products to the liquid water in the chamber and to the solvent with captured carbon dioxide conveyed through the first heat exchanger of the chamber.

In still another embodiment, a method includes receiving a hydrocarbon combustion exhaust stream including at least water and carbon dioxide in a chamber containing liquid water. The liquid water, in an exemplary embodiment including water condensed from the combustion exhaust stream, in the chamber is subjected to electrolysis to generate hydrogen and oxygen. Methanation reaction products are passed through a heat exchanger of the chamber to transfer heat from the methanation reaction products to the liquid water. Carbon dioxide is captured in a solvent, and the solvent with the captured carbon dioxide is heated in the same or a different heat exchanger of the chamber. At least a portion of the carbon dioxide is separated from the heated solvent. The hydrogen generated by the electrolysis and the carbon dioxide separated from the heated solvent are reacted in a methanation reactor to generate one or more hydrocarbons, such as methane.

In a further embodiment, a system includes a chamber, an electrolysis system, and one or more heat exchangers. The chamber is configured to contain liquid water and to receive a hydrocarbon combustion exhaust stream including at least water and carbon dioxide. The electrolysis system is configured to generate hydrogen and oxygen, and includes at least an anode and a cathode each received in the chamber. The one or more heat exchangers is/are positioned in the chamber and configured to convey methanation reaction products through the chamber to transfer heat from the methanation reaction products to the liquid water.

In still a further embodiment, a system includes a chamber, a carbon dioxide absorber, and first and second heat exchangers. The chamber is configured to subject liquid water to electrolysis to generate hydrogen and oxygen. The carbon dioxide absorber is configured to capture carbon dioxide in a solvent. The first heat exchanger is positioned in the chamber and configured to convey the solvent and the captured carbon dioxide through the chamber. The second heat exchanger, which may be the same as or different than the first heat exchanger, is positioned in the chamber and configured to convey methanation reaction products through the chamber to transfer heat from the methanation reaction products to the liquid water in the chamber and to the solvent with captured carbon dioxide being conveyed through the first heat exchanger of the chamber.

According to another embodiment, a system includes a chamber configured to contain liquid water and to receive a hydrocarbon combustion exhaust stream including at least water and carbon dioxide. An electrolysis system comprising an anode and a cathode positioned in the chamber is configured to generate hydrogen and oxygen from the liquid water. A first heat exchanger is positioned in the chamber and configured to convey methanation reaction products through the chamber to transfer heat from the methanation reaction products to the liquid water. A carbon dioxide absorber is configured to capture the carbon dioxide in a solvent. A second heat exchanger, which may be the same as or different than the first heat exchanger, is positioned in the first chamber and configured to heat the solvent and the captured carbon dioxide with thermal energy from the methanation reaction products. A carbon dioxide desorber is configured to separate at least a portion of the carbon dioxide from the heated solvent. A methanation reactor is configured to react at least the hydrogen generated by the electrolysis system and the carbon dioxide separated from the heated solvent to generate one or more hydrocarbons.

Other aspects of the invention, including apparatus, devices, systems, sub-systems, assemblies, sub-assemblies, processes, methods, and the like, which constitute part of the invention, will become more apparent upon reading the following detailed description of the exemplary embodiments.

BRIEF DESCRIPTION OF THE DRAWINGS

The accompanying drawings are incorporated in and constitute a part of the specification. Features shown in the drawings are meant as illustrative of only some embodiments, and not of all embodiments, unless otherwise explicitly indicated. In such drawings.

DETAILED DESCRIPTION OF THE EXEMPLARY EMBODIMENTS AND EXEMPLARY METHODS

It will be readily understood that the components, structures, and features of the present embodiments, as generally described and illustrated in the Figures incorporated herein, may be arranged and designed in a wide variety of different configurations. Thus, the following detailed description of the embodiments of the apparatus, system, and method of the present embodiments, as presented in the Figures, is not intended to limit the scope of the embodiments, as claimed, but is merely representative of selected embodiments.

Reference throughout this specification to "a select embodiment," "an embodiment," "an exemplary embodiment," "one embodiment," or "at least one embodiment" means that a particular feature, structure, or characteristic described in connection with the embodiment is included in at least an embodiment. Thus, appearances of the phrases "a select embodiment," "an embodiment," "an exemplary embodiment," "in one embodiment," or "in at least one embodiment" in various places throughout this specification are not necessarily referring to the same embodiment or different embodiments. The various embodiments may be combined with one another in various combinations that would be understood to those skilled in the art having reference to this disclosure.

The illustrated embodiments will be best understood by reference to the drawings, wherein like parts are designated by like numerals throughout. The following description is intended only by way of example, and illustrates certain selected embodiments of systems, processes, and apparatuses that are consistent with the certain selected embodiments.

Figure 1:
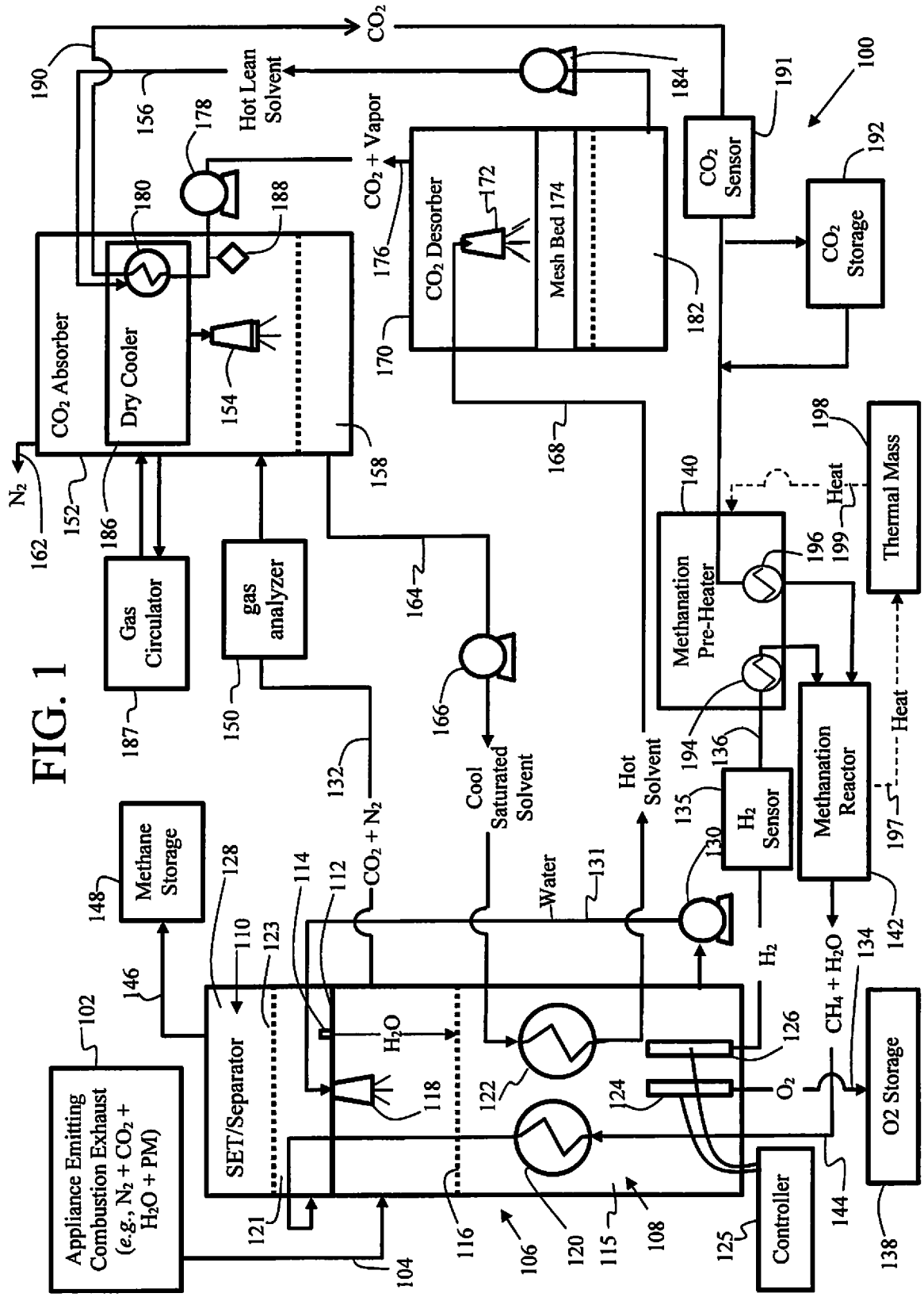
FIG. 1 is a schematic flow diagram of a system according to an exemplary embodiment.
Figure 2:
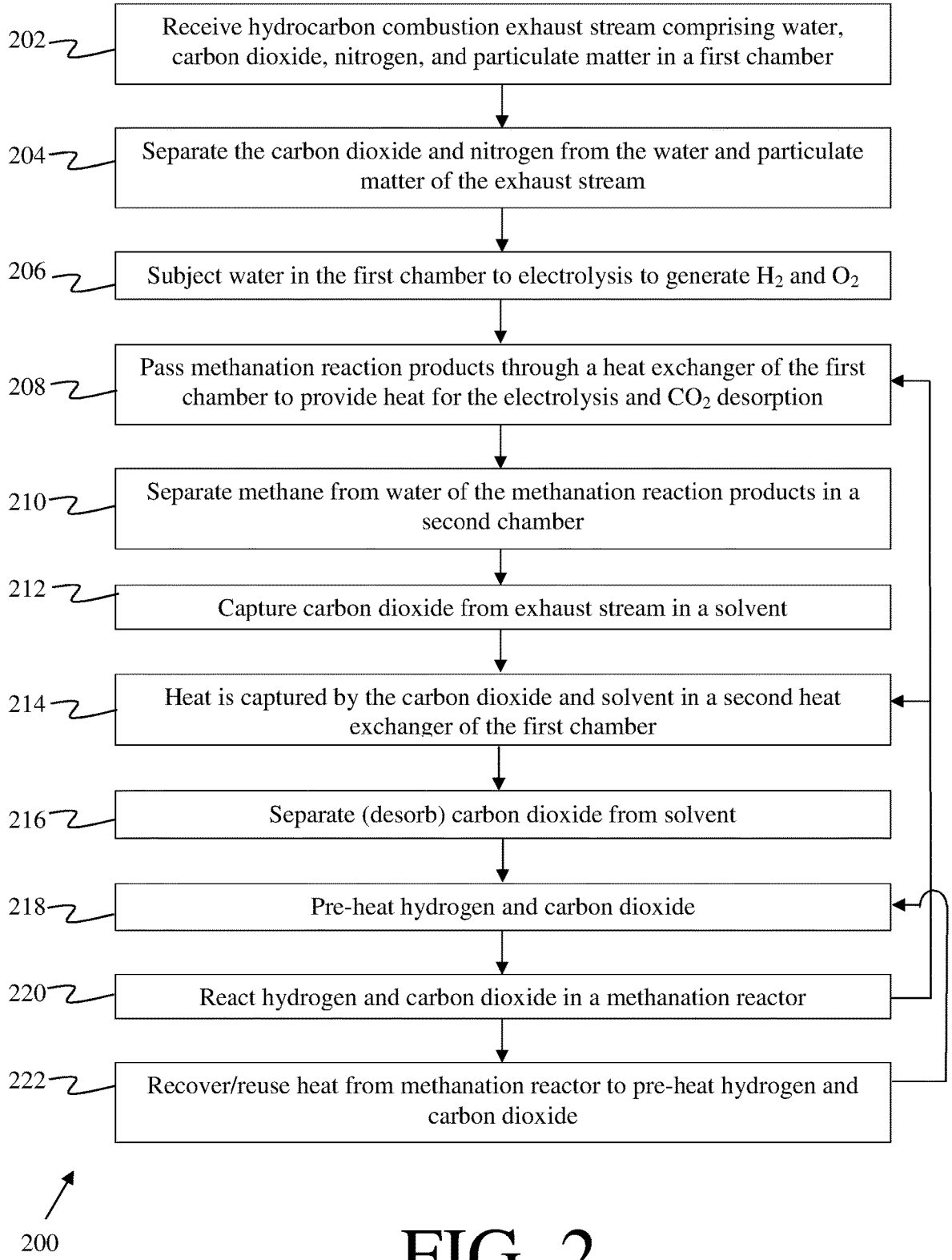
FIG. 2 is a flow chart of a method according to an exemplary embodiment.

Exemplary embodiments are now described with respect to a system (100) of FIG. 1 and a process (200) of FIG. 2.

In step (202) of the flowchart (200) of FIG. 2, a hydrocarbon combustion exhaust stream that has undergone at least partial (or substantially complete or complete) combustion is received. The stream may originate from various resources, such as, without limitation, one or more hydrocarbon combustion appliances and/or plants, such as an electricity generation plant. Combustion of hydrocarbons is the basis for most processes and systems that underpin modern economies. Combustion equipment includes, but is not limited to, boilers for producing hot water and steam, furnaces for producing hot air, internal combustion engines for vehicles in transportation, turbines for power generation and jet propulsion, rocket nozzles for missile and spacecraft thrust, industrial kilns, smelting processes for producing steel, etc. These apparatuses exhaust mixtures typically including carbon dioxide, water, nitrogen, trace gases (e.g., carbon monoxide, nitrogen oxides, sulfur oxides, argon, etc.), or combinations thereof, and particulate matter (e.g., soot), typically as a result of combustion. Carbon dioxide and water typically compose, for example, more than 99% by mass of the total mass of the non-nitrogen portion of the exhaust during the combustion of hydrocarbons and air. Carbon monoxide may be present in significantly smaller quantities depending on the excess air ratio used during combustion. The ratios may vary according to the combustion process and input material.

The system (100) of FIG. 1 includes a combustion reactor or other appliance (102) from which an exhaust stream (also referred to herein as a combustion stream and the like) (104) is received. The combustion appliance (102) typically burns a hydrocarbon such as methane in the presence of an oxygen source such as air, emitting the exhaust stream (104) typically containing carbon dioxide, nitrogen, and water, which may be present in various physical forms, such as steam, vapor, and liquid, but typically is mostly if not entirely gaseous. Exemplary embodiments are designed to handle mixed exhaust streams comprising some or all of the constituents described above and other constituents, e.g., particulate matter.

According to an embodiment, the exhaust stream (104) leaves the combustion appliance (102) and is received in step (202) at a temperature of, for example, approximately 100° C. to 350° C., such as, for example about 250° C. The exhaust stream (104) typically contains gaseous water in an amount of, for example, as much as 10 percent by mass based on the total mass of the exhaust stream (104).

The exhaust stream (104) is introduced into a tank or the like, generally designated by reference numeral (106), also referred to herein as a SET/separator tank (106). The SET/separator tank (106) contains a first (shown as a lower) chamber (or compartment) (108), also referred to herein as the SET chamber or the SET tank, and a second (shown as an upper) chamber (or compartment) (110), also referred to herein as the methane separation chamber or the methane separation tank. For the purposes of this application, SET is an acronym that stands for Scrubbing, Electrolysis, and Transfer of heat.

The SET chamber (108) and the methane separation chamber (110) are partitioned by a non-permeable partitioning wall (112), which is shown extending horizontally in FIG. 1, but may possess other orientations. The partitioning wall (112) includes an injection tube or port (114) that fluidly communicates the SET chamber (108) and the methane separation chamber (110) with one another. While the SET chamber (108) and the methane separation chamber (110) are shown in FIG. 1 as being part of a common, that is the same, equipment or tank (106), in another embodiment the SET chamber (108) and the methane separation chamber (110) may be embodied as different pieces of equipment, such as a SET tank and a separate and discrete separator tank. Alternatively, the positioning of the chambers (108) and (110) may be reversed or switched with respect to one another.

FIG. 1 illustrates the exhaust stream (104) being fed into the SET chamber (108) containing a liquid (115), which in an exemplary embodiment includes or is composed of water. As shown, in an embodiment the exhaust stream (104) is fed into a space (also referred to as a headspace) of the SET chamber (108) above a liquid level line (116). In embodiments, the liquid (115) establishing the liquid level line (116) includes or is substantially entirely water, optionally containing other liquids and/or particulate matter (e.g., soot) from the exhaust stream (104). The liquid (115) in the SET chamber (108) may include other materials, such as solids (e.g., particulates) and buffers (e.g., KOH), e.g., for counteracting pH changes caused by acids, if any, formed from components of the exhaust stream (104). The particulate matter is trapped or entrained within the liquid (115), and may be removed via periodic cleaning.

The SET chamber (108) further includes a spray mechanism (118), a first heat exchanger (120), a second heat exchanger (122), and an electrolysis cell (unnumbered in FIG. 1) including an electrolysis anode (124), an electrolysis cathode (126), and a controller (125). The first and second heat exchangers (120) and (122), respectively, may be separate heat exchangers or a common (i.e., the same) heat exchanger, as shown, for example, in the embodiment of FIG. 3, discussed below. The terms "first" and "second" in this regard are not used to designate sequence or order of steps or importance. The terms "first" and "second" are interchangeable, i.e., the heat exchanger (122) may be designated "first" and the heat exchanger (120) may be designated "second," generally depending upon the order in which the heat exchangers are described in this specification or recited in the claims.

As the combustion stream (104) is received in the SET chamber (108), the combustion stream (104) is subject to cooling (or thermal transfer) by passing the combustion stream (104) under the spray mechanism (118), which may be embodied as a nozzle, an atomizer, or other equipment for contacting the liquid discharged by the spray mechanism (118) with the incoming combustion stream (104). The liquid, typically mostly or all water, from the spray mechanism (118) condenses a portion or all of the gaseous water entrained in the incoming combustion stream (104) and optionally acts as a scrubber to remove entrained particulate matter (e.g., soot) from the incoming combustion stream (104) and into the liquid (115). In an embodiment, substantially all of the gaseous water entrained in the combustion stream (104) is condensed, such that the only remaining water, if any, in the gas stream leaving the SET tank (108) via line (132) is due to the inherent vapor pressure of water in the gas stream at its given temperature, for example, approximately 80° C. In an embodiment, the water entrained in the gas leaving the SET tank (108) via the line (132) is in the form of vapor as opposed to the water in the inlet stream (104) that was in the form of saturated or super-heated steam. In an embodiment, additional water purification steps within the SET tank (108), such as before electrolysis (discussed below), are not required and may be omitted (but are not precluded). Transfer lines such the line (132) described above other lines described below are also interchangeably referred to herein as conduits.

Water (or other liquid) emitted from the spray mechanism (118) and the water condensed from the combustion stream (104) are collected at the lower part of the SET chamber (108), as represented in FIG. 1 by the liquid (115) and the water/liquid level line (116). In an embodiment, the incoming combustion stream (104) is cooled to about 80° C. by the water or other liquid from the spray mechanism (118). In an embodiment, a portion of the water or other liquid emitted by the spray mechanism (118) is fed via a pump (130) and conduit (131) from the lower part of the SET chamber (108) into the methane separation chamber (110) for further use and processing, as described below.

The carbon dioxide and nitrogen of the combustion stream (104) are discharged from the SET chamber (108) via the line (132). Accordingly, the carbon dioxide is thereby separated from the water of the combustion stream (104) in order to obtain relatively pure carbon dioxide and nitrogen for later processing, including in certain embodiments absorption, desorption, and methanation, as discussed in greater detail below. In an exemplary embodiment, the resulting gas mixture in the line (132) is substantially or fully dry or water free. In exemplary embodiments, the resulting gas mixture contains 0 to about 3 weight percent water, 0 to about 2 weight percent water, or 0 to about 1 weight percent water, or less than 0.1 weight percent water. Separation of the water entrained in the incoming combustion stream (104) from the carbon dioxide at an early stage in the system (100) and process (200) is desirable because the carbon dioxide is later subjected to a methanation reaction (described below). Water, if not removed, would inhibit the methanation reaction, given that water is one of reaction products of methanation, as shown the equation below. Thus, unremoved water (if any) that makes its way to the reactor pushes the rate constant to the left and decreases the kinetic reaction rate.

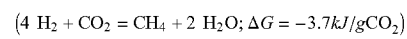

$$(4\ H_2 + CO_2 = CH_4 + 2\ H_2O;\ \Delta G = -3.7 kJ/gCO_2)$$

As mentioned above, in an exemplary embodiment electrolysis is carried out in the SET chamber (108) using the anode (124) and the cathode (126) to generate hydrogen and oxygen (206). The anode (124) and the cathode (126) are shown operatively connected to the electrolysis system controller (125), e.g., the electrically communicate with the controller (125). In non-limiting embodiments, the electrolysis equipment (124)-(126) may be, for example, part of an alkaline, PEM, or radio-wave electrolysis system. Electrolysis uses electricity to split water in the SET chamber (108) into oxygen and hydrogen. The water used for the electrolysis is supplied, in part or completely, from the exhaust combustion stream (104), which acts as a feedstock for the electrolysis. The oxygen and hydrogen produced by electrolysis are discharged from the SET chamber (108) via lines (134) and (136), respectively. The lines (134) and (136), as well as other lines and conduits described herein, may be, for example, piping, hoses, tubes, etc. In an exemplary embodiment, an example of which is discussed below with reference to FIG. 3, neither the line (134) nor the line (136) leaving the electrolysis cell pass through the fluid (e.g., water) (115) outside of the electrolysis cell. For example, in FIG. 3, lines (334) and (336) (corresponding to lines (134) and (136), respectively, of FIG. 1) exit an electrolysis cell (305) above a liquid (e.g. water) level line (316) corresponding to liquid level line (116) of FIG. 1.

In an embodiment, the production of hydrogen via electrolysis can be selectively throttled based on the supply of affordable electricity. In an embodiment, the electrolysis system controller (125) is connected in real-time via the Internet to real-time electricity markets and/or the performance of distributed electricity generation equipment. The connected controller (125) is configured to decide, e.g., based on project-specific economic parameters, whether to open or close an electrical switch that manages the supply of electricity for carrying out the electrolysis.

According to an embodiment, the SET chamber (108) is operated in accordance with a SET tank steady state equation as follows:

$$0 = \dot{m}_s(h_{in} - h_{out})_s + \dot{Q}_{elec} + \dot{Q}_{ex} + (\dot{m}h)_{r,in} - (\dot{m}h)_{r,out} + \dot{m}_{H2O,cond} h_{fg,H2O}$$

wherein $\dot{m}_s$ is the mass flow rate of the solution ($H_2O$+MEA) going into (164) the SET tank (108) and leaving (168) the SET tank (108), $(h_{in} - h_{out})_s$ is the specific enthalpy difference of the solvent before entering (164) and after exiting (168) the SET tank (108), $(\dot{m})_{r,in}$ is the inlet mass flow rate of the methanation products (144) ($CH_4 + 2H_2O$), $(h)_{r,in}$ is the inlet specific enthalpy of the methanation products (144) ($CH_4 + 2H_2O$), $(\dot{m})_{r,out}$ is the mass flow rate of the methane (146), $(h)_{r,out}$ is the specific enthalpy of the methane (146), $\dot{m}_{H2O,cond}$ is the mass flow rate of condensate (114), $h_{fg,H2O}$ is the latent heat from H2O condensation (114), $\dot{Q}_{ex}$ is the heat produced by the combustion exhaust leaving the generator, boiler, or other example combustion appliance (104), and $\dot{Q}_{Elec.}$ is the heat produced by the electrolysis.

As an example of a theoretical application of the SET tank steady state equation, the following assumptions are made: (1) 10 kW petrol generator, boiler, etc. with 70% efficiency, 1.5 g/s exhaust gas flow rate, 15% carbon dioxide (CO2) mass fraction. (2) 100% $CO_2$ capture and conversion into methane (CH4). (3) 10 kW electrolysis system cycle that operates 50% of the time, with 50% efficiency. Also, the following conditions are assumed: (1) inlet solvent (164) temperature and pressure are 300K and 1.5 bar, respectively, and (2) outlet solvent (168) temperature and pressure are 360K and 1.5 bar, respectively (assuming zero pressure drop).

In a theoretical example, the SET tank steady state equation is solved for the mass flow rate of the solution entering (164) the SET tank as follows:

$$\dot{m}_s = \frac{\left[ \dot{Q}_{elec} + \dot{Q}_{ex} + (\dot{m}h)_{r,in} - (\dot{m}h)_{r,out} + (\dot{m}_{H2O,cond} \cdot h_{fg,H2O}) \right]}{(h_{out} - h_{in})_s}$$

wherein $$\dot{Q}_{elec} = \frac{10 \text{ kW} \cdot 50\%}{2} = 2.5 \text{ kW};$$

$$\dot{Q}_{ex} = \frac{10 \text{ kW}}{70\%} = 14.3 \text{ kW};$$

$(\dot{m})_{r,in}$ (623K, 1.5 bar)=0.27 g/sec; $(h)_{r,in}$ (623K, 1.5 bar)=2,754 kJ/kg; $\dot{m}_{H2O,cond}$=0.19 g/s; $h_{fg,H2O}$=2,200 kJ/kg; $(\dot{m})_{r,out}$=0.26 g/sec; $(h)_{r,out}$ (300K, 1.5 bar)=1,419 kJ/kg; and reactor heat transfer=$(\dot{m}h)_{r,in} - (\dot{m}h)_{r,out} + (\dot{m}_{H2O,cond} \cdot h_{fg,H2O})$=0.7 kW;

$$h_{out} = 242 \frac{kJ}{kg};$$

$$h_{in} = 7 \frac{kJ}{kg}.$$

Solving for $\dot{m}_s$, $$\dot{m}_s = \frac{[2.5 \text{ kW} + 14.3 \text{ kW} + 0.7 \text{ kW}]}{\left(242 \frac{kJ}{kg} - 7 \frac{kJ}{kg}\right)_s} = 0.075 \frac{kg}{s}$$

In the embodiment illustrated in FIG. 1, oxygen is fed via the line (134) to an oxygen storage tank (138). Alternatively, the line (134) may deliver the oxygen back to the appliance (102), to another appliance (not shown), or may be used for other purposes. The hydrogen is fed via the line (136) from the SET chamber (108) to a methanation pre-heater (140). A pressure transducer (or hydrogen sensor) (135) (the equivalent of Pressure trans 2 (520) in FIG. 5 and PT-2 (612) in FIG. 6, discussed below), is positioned along the feed line (136) for measuring the overall pressure in the line/reactor that is inclusive of all gases that may be present. As an example, the pressure may be in a range of 0 bar to 10 bar. As a non-limiting example, 0.1 to 0.5 bar of negative pressure (less than 1 bar) may be used to aspirate the hydrogen out of the SET chamber (108). The pressure transducer (135) is labeled as an $H_2$ sensor in FIG. 1 in order to reflect the typical operating conditions, where the only constituent within the conduit will be (or is assumed to be) hydrogen and therefore a change in pressure will reflect a change in the presence of hydrogen within the conduit.

If needed or desired, an additional amount of water (or "make-up water") can be added to the SET chamber (108) from the methane separation chamber (110) via the injection conduit or port (114) to increase the hydrogen and oxygen production in the SET chamber (108). As mentioned above in connection with the spray mechanism (118), a portion of the water or other liquid in the methane separation chamber (110) is delivered to the methane separation chamber (110) by the pump (130) and conduit (131). Another portion of the water or other liquid in the methane separation chamber (110) is supplied from a methanation reactor (142) via conduit (144), as will be described in greater detail below. The water in the methane separation chamber (110) is also referred to herein as condensate (121), which defines a condensate level line (123).

The conduit (144), e.g., one or more sealed tubes, carries methanation reaction products, including methane and gaseous water, into the SET chamber (108) and through the first heat exchanger (120) located in the SET chamber (108). The first heat exchanger (120) may be embodied as one or more sealed pipes and/or coils carrying the methanation reaction products through the liquid (e.g., water) (115) in the SET chamber (108) to cause heat transfer from the methanation reaction products to the liquid (115). In another embodiment, known and other heat exchangers may be used as the first heat exchanger (120). The methane reaction products generally have a relatively high temperature, for example, in a range of 150° C. to 450° C., compared to the water (115) in the SET chamber (108).

The transfer of heat from the reaction products in the conduit (144) to the water or other liquid (115) in the SET chamber (108) facilitates electrolysis (206), described above, and solvent heat (214) and carbon dioxide desorption (216), described below. In an exemplary embodiment, electrolysis takes place at about 80° C. The methanation reaction products in the conduit (144) are cooled by the water (115) in the SET chamber (108), e.g., to about 80° C., and are delivered into the methane separation chamber (110). According to an embodiment, the conduit (144) delivers the methanation reaction products below the condensate level line (123) of the condensate (121) of the methane separation chamber (110). According to another embodiment (not shown), the conduit (144) delivers the methanation reaction products above the condensate level line (123) of the condensate (121), i.e., into the headspace of the chamber (110).

Methane is separated (210) from the water and any particulate matter in the methane separation chamber (110) via condensation of the water (and gravity), which forms the condensate (121). The separated methane is delivered via conduit (146) to a methane storage tank (148). In an embodiment, the system (100) further includes a compressor configured to pressurize the methane to an ideal storage pressure of, for example, as much as 200 bar, for delivery to the methane storage tank (148). The methane gas may be stored in the methane storage tank (148) for a finite period or an indefinite time period, such as long as multiple years, if desired or required. The methane that is produced may be stored indefinitely and has an energy density of, for example, more than 100 times that of a typical lithium-ion battery, which makes the methane a practical medium for serving as the basis for an economy that runs 100% on renewable energy. The methane stored in the tank (148) may be burned in the presence of air for various uses, including, without limitation, use in the combustion appliance (102), heat production, electricity production, or mechanical energy.

In an embodiment, the concentration (e.g., mass percent) of the carbon dioxide in the conduit (132) is measured by a gas analyzer (150) before the carbon dioxide and nitrogen are fed into a carbon dioxide absorber (152). In an embodiment, the gas analyzer (150) is configured to use electromagnetic wave profiles to determine carbon dioxide concentration (e.g., mass percent) in the gas stream within the conduit (132). In embodiments, the measured carbon dioxide concentration may be used to determine speeds of pumps and fans that drive the absorber (152) and a desorber, also referred to as a regenerator, (170) and/or measuring the overall efficiency of carbon dioxide capture.

The carbon dioxide absorber (152) is operable to separate the carbon dioxide from the nitrogen and any other gases (e.g., carbon monoxide), which if present, are typically in trace amounts. In an embodiment, the carbon dioxide and nitrogen are injected in the carbon dioxide absorber (152) under a spray mechanism (e.g., a nozzle, atomizer, etc.) (154) that sprays a carbon dioxide solvent (delivered via (156), discussed below). In an exemplary embodiment, the spray mechanism (e.g., nozzle) (154) delivers the solvent as a fine mist. The carbon dioxide solvent is combined with the carbon dioxide and nitrogen in order to capture (or absorb) the carbon dioxide (212), in an exemplary embodiment to saturation. Representative solvents for carbon dioxide capture include, for example, monoethanolamine (MEA), Selexol® (dimethyl ethers of polyethylene glycol (DEPG)), Fluor solvent (propylene carbonate), Purisol (N-methl-2-pyrrolidone), Rectisol (methanol), a sulfinol solvent (a mixture of diisopropanolamine or methyl diethanolamine (MDEA), sulfinol (containing sulfolane, tetrahydrothiophene dioxide and water), econamine FG (amine-based), and ionic liquids (e.g., 1-butyl-3-propylamineimidazolium tetrafluoroborate). In an exemplary embodiment, the solvent comprises a sulfinol solvent or an equivalent solvent. Temperature in the absorber (152) may be conducive to capturing the carbon dioxide in the solvent. In an exemplary embodiment, a temperature of, for example, 20° C. is useful for carbon dioxide capture, although room temperature and other temperatures may be used.

The resulting solvent with captured carbon dioxide falls via gravity to the bottom chamber (158) of the absorber (152) where the solvent collects. In an embodiment, the relatively cool solvent is saturated with the carbon dioxide at this point. The nitrogen and any trace gases in the absorber (152) are vented (162) from the top of the absorber (152) into the atmosphere or collected (not shown). Nitrogen is a non-polar diatomic molecule that typically does not chemically bind to the solvent, whereas the carbon dioxide does, thus explaining why the nitrogen is not captured by the solvent falling into the bottom chamber (158) of the absorber (152). The mechanism for the capture of carbon dioxide by the solvent is unique to each solvent. For example, in the case of MEA, without wishing to be bound by any theory, the capture mechanism is believed to involve hydrogen bonding. Without wishing to be bound by any theory, in the case of the above-mentioned embodiment with sulfinol, the mechanism is related to the bonding between the hydrogen atoms in the sulfinol to the atoms in the carbon dioxide.

According to an embodiment, the carbon dioxide absorber (152) is operated in accordance with the absorber energy balance equation as follows:

$$0 = \dot{Q}_{Abs} + (\dot{m}h)_{ex,in} + \dot{m}_{vap}(h_{in} - h_{out})_{vap} + \dot{m}_s(h_{in} - h_{out})_s + \dot{m}_{air}(h_{in} - h_{out}) - (\dot{m}h)_{N2,out}$$

wherein $(h)_{ex,in}$ is the exhaust gas inlet enthalpy (132), $(\dot{m})_{ex,in}$ is the exhaust gas inlet mass flow rate (132), $\dot{m}_{vap}$ is the mass flow rate of the $CO_2 + H_2O$ vapors post the desorber and the outlet mixture after the dry cooler (176), $(h_{in} - h_{out})_{vap}$ is the specific enthalpy difference between the $CO_2 + H_2O$ vapors post the desorber (176) and the outlet mixture after the dry cooler (186), $\dot{m}_s$ is the mass flow rate of the lean amine (solvent inlet) (156) or the saturated amine (solvent outlet) (164), which should be substantially equal to one another, $(h_{in} - h_{out})_s$ is the enthalpy difference between the lean amine (solvent inlet) (156) and the saturated amine (solvent outlet) (164), $\dot{m}_{air}$ is the mass flow rate of the inlet air or the outlet air (187), which should be substantially equal to one another, in the dry cooler (186), $(h_{in} - h_{out})$ is the enthalpy difference between the inlet air and the outlet air (187) in the dry cooler (186), $(\dot{m})_{N2,out}$ is the mass flow rate of the non-captured gas (162) that leaves the absorber (152), and $(h)_{N2,out}$ is the specific enthalpy of the non-captured gas (162) that leaves the absorber (152), and $\dot{Q}_{Abs}$ is the heat of absorption (152).

As an example of a theoretical application of the carbon dioxide absorber equation, the following theoretical assumptions are made: (1) an adiabatic absorption tower as the absorber (152), (2) assume no heat transfer in the dry cooler (i.e., no difference in the captured gas enthalpy and the exhaust gas enthalpy), (3) heat generation is due to absorption only, and (4) carbon dioxide capture flow rate is 0.5 g/s. Additionally, the following conditions are assumed: (1) inlet solvent temperature and pressure are 300K and 1.5 bar, respectively, (2) solvent mass flow rate is 0.1 kg/sec, and (3) the heat of absorption is $$1820 \frac{kJ}{kg - CO_2}.$$

In a theoretical example, the absorber energy balance equation is solved for outlet solvent temperature as follows, wherein $c_p$ is the heat capacity of the solvent:

$$0 = \dot{Q}_{Abs} + \dot{m}_s(h_{in} - h_{out})_s$$

$$h_{out} = \frac{\dot{Q}_{Abs}}{\dot{m}_s} + h_{in} = \frac{1820 \cdot 0.5 \cdot 10^{-3}}{0.1} + 7 \frac{kJ}{kg} = 16.1 \frac{kJ}{kg}$$

$$T_{out} = T_{in} + \frac{\Delta h}{c_p} = 300 + \frac{16.1 - 7}{3.88} = 302.34$$

The relatively cool solvent, which in an exemplary embodiment is saturated or substantially saturated with the captured carbon dioxide, is directed out of the absorber (152) via conduit (164) by a pump (166). The solvent with captured carbon dioxide within the conduit (164), e.g., sealed tube(s), is passed through the second heat exchanger (122) in the SET chamber (108). The second heat exchanger (122) may be embodied as one or more sealed pipes and/or coils carrying the solvent with captured carbon dioxide through the water (115) or other liquid in the SET chamber (108) to cause heat transfer. In another embodiment, known and other heat exchangers may be used as the second heat exchanger (122). The first and second heat exchangers (120) and (122), respectively, may be a single (common) heat exchanger or different heat exchangers. The solvent with captured carbon dioxide is heated (214) in the SET chamber (108). In an exemplary embodiment, heat released by the methanation reaction products from the first heat exchanger (120) into the liquid (115) is used to heat the solvent with the captured carbon dioxide. In an embodiment, the solvent with captured carbon dioxide is heated to about 80° C. The heated solvent with the carbon dioxide are conveyed out of the SET chamber (108) along conduit (168) to the carbon dioxide desorber (170).

In an embodiment of an operation of the carbon dioxide desorber (170), the heated solvent with captured carbon dioxide is sprayed through a spray mechanism (172), such as a nozzle, atomizer, etc., onto a mesh bed (174). In an embodiment, the mesh bed comprises a physical contact materials used in gas and/or liquid reactors to increase the surface available for absorption and/or chemical reactions. In an embodiment, the mesh bed is designed to possess high surface area and low pressure drop characteristics and is made of a chemically inert material or materials. The carbon dioxide and water vapor, to the extent that any such vapor has been captured by the solvent, are released from the heated solvent due to the high temperature in a carbon dioxide desorption or reclamation step (216), and are allowed to vent out of the carbon dioxide desorber (170) through a conduit (176).

The carbon dioxide and vapor are pumped via a pump (178), which in an embodiment may be a fan or blower operating to maintain movement of the carbon dioxide and any vapor, to a third heat exchanger (180). The unsaturated hot solvent in the carbon dioxide desorber (170) falls via gravity to a bottom chamber (182) of the desorber (170).

According to an embodiment, the desorber (152) is operated in accordance with the desorber energy balance equation below:

$$0 = \dot{Q}_{Des} + \dot{m}_{in}^{Sat} \cdot h_{in}^{Sat} - \dot{m}_{out}^{CO2} h_{out}^{CO2} - \dot{m}_{out}^{MEA} h_{out}^{MEA}$$

wherein $\dot{Q}_{Des}$ is the heat consumed by desorption,
$\dot{m}_{in}^{Sat.}$ is the mass flow of saturated MEA (or other solvent) solution entering (168) the desorber (170),
$h_{in}^{Sat}$ is the specific enthalpy of the saturated MEA (or other solvent) solution entering (168) the desorber (170) at 87° C. and 1 bar,
$\dot{m}_{out}^{CO2}$=the mass flow of the CO2 exiting (176) the desorber (170),
$h_{out}^{CO2}$=the specific enthalpy of the CO2 exiting (176) the desorber (170) at 87° C. and 1 bar,
$\dot{m}_{out}^{MEA}$=the mass flow unsaturated MEA (or other solvent) leaving (156) the desorber (170), and
$h_{out}^{MEA}$=the specific enthalpy of the MEA (or other solvent) leaving (156) the desorber (170) at 87° C. and 1 bar.

As an example of a theoretical application of the desorber energy balance equation, the following assumptions are made: (1) an adiabatic desorption tower, (2) assuming no carbon dioxide and vapor enthalpies (3) heat generation is due to desorption only, and (4) carbon dioxide capture flow rate is 0.5 g/s. Additionally, the following conditions are assumed: (1) inlet solvent temperature and pressure are 360K and 1.5 bar, respectively, (2) solvent mass flow rate is 0.1 kg/sec, and (3) the heat of absorption is $$1820 \frac{kJ}{kg - CO_2}.$$

In a theoretical example, the desorber energy balance equation is solved for outlet solvent temperature as follows:

$$0 = \dot{Q}_{Des} + \dot{m}_{in}^{Sat} \cdot h_{in}^{Sat} - \dot{m}_{out}^{MEA} h_{out}^{MEA}$$

$$h_{out}^{MEA} = -\frac{\dot{Q}_{Des} \cdot \dot{m}_{out}^{CO2}}{\dot{m}_{out}^{MEA}} + h_{in}^{Sat} = -\frac{1820 \cdot 0.5 \cdot 10^{-3}}{0.1} + 242 \frac{kJ}{kg} = 233 \frac{kJ}{kg}$$

In FIG. 1, a pump (184) transports the unsaturated hot solvent along the conduit (156) to a dry cooler (186) that forms part of or includes the third heat exchanger (180). A gas circulator (187) is shown operatively connected to the dry cooler (186) for transporting gas to and from the dry cooler (186) and the third heat exchanger (180). In an exemplary embodiment, the gas circulated by the gas circulator (187) is air. In an embodiment, the gas circulator (187) pulls room temperature air from the surrounding embodiment, as needed or desired. The third heat exchanger (180) causes an exchange of heat between, on the one hand, the carbon dioxide and water vapor from conduit (176) and the hot unsaturated solvent from the conduit (156), and on the other hand, the cool gas (e.g., air) cycled through by the gas circulator (187). As the carbon dioxide and water vapor cool, condensate from the water vapor is collected in collection vessel (188). The solvent from the conduit (156), now cooled, is fed to and discharged through the nozzle (154) as described above for again capturing carbon dioxide fed into the carbon dioxide absorber (152) via the conduit (132).

The carbon dioxide is transported from the third heat exchanger (180) along conduit (190) to the methanation pre-heater (140). The conduit (190) carrying the carbon dioxide is shown equipped with a carbon dioxide ($CO_2$) sensor (191). In an embodiment, the carbon dioxide sensor (191) measures the content (e.g., mass percentage or mass flow of $CO_2$) of carbon dioxide in the conduit (190). Excess carbon dioxide may be stored in a carbon dioxide storage tank (192) for later use, including later feeding to the methanation pre-heater (140).

The methanation pre-heater (140) includes fourth and fifth heat exchangers (194) and (196), respectively, for pre-heating (218) the hydrogen delivered via conduit (136) and the carbon dioxide delivered via conduit (190), respectively. In an embodiment, a thermal mass (198) serves as a heat source, delivering thermal energy to the fourth and fifth heat exchangers (194) and (196), respectively. In an exemplary embodiment, the thermal mass (198) is heated by the exothermic reaction that takes place in the methanation reactor (142), as described in further detail below. As shown in FIG. 1, the thermal mass (198) is positioned external to the methanation reactor (142) in accordance with the illustrated embodiment. In another embodiment (not shown), the thermal mass (198) is positioned within or internal to the methanation reactor (142). In still another embodiment (not shown), first and second thermal masses are respectively positioned internal and external to the methanation reactor (142). In an embodiment, the thermal mass (198) comprises a phase change material such as sodium nitrate ($NaNO_3$).

Carbon dioxide and hydrogen pre-heated by the methanation pre-heater (140) are introduced into the methanation reactor (142), where the carbon dioxide and hydrogen react to generate combustible hydrocarbons, in particular at least methane, and water (220). A Sabatier reactor may be used as the methanation reactor (142). In an exemplary embodiment, the reactor (142) is maintained at a temperature or temperatures in a range of 150° C. and 400° C., typically about 350° C. An appropriate catalyst, such as nickel, may be used to initiate a Sabatier reaction to produce the methane and water from the carbon dioxide and hydrogen.

In step (222), waste heat from methanation reactor (142) is recovered and reused. In the illustrated system (100), the waste heat is conveyed via line (197) to the thermal mass (198), which may be internal or external to the methanation reactor (142). In an embodiment, the thermal mass (198) is melted by the heat released by the exothermic reaction between carbon dioxide and hydrogen in the methanation reactor (142). In an exemplary embodiment the methanation reactor (142) operates at a minimum temperature of 150° C., and typically operates at a temperature of 350° C.

The high temperature methane and gaseous water generated in step (220) are discharged from the methanation reactor (142) via the conduit (144), which as described above enters the SET chamber (108) and the first heat exchanger (120) to provide heat for electrolysis and/or carbon dioxide desorption, as represented in FIG. 2 by the return arrow from step (220) to step (208).

It should be understood that the illustrated system (100) of FIG. 1 may be altered or modified in various manners. Additional conduits, pumps, sensors, valves, other equipment, etc. may be added to the system (100). Further, one or more conduits, pumps, sensors, valves, other equipment, etc. illustrated in FIG. 1 may be omitted from the system (100). Modifications may be made to the flow paths and arrangement of conduits, pumps, sensors, valves, other equipment, etc.

In an exemplary embodiment, part or all of the system (100), including the operation of the carbon dioxide absorber (152) and carbon dioxide desorber (170), is continuous and carried out on a constant basis. In other embodiments, parts or all of the system (100), such as methanation (220), may be carried out in batch mode.

In an exemplary embodiment, the system (100) is a closed loop thermal and hydrogen management system that integrates carbon dioxide capture and release, electrolysis, and methanation. In exemplary implementations, hydrogen is conserved and thermal energy is efficiently used and recycled. In an exemplary implementation, pollution (e.g., the exhaust stream (104)) is converted into natural gas (methane) in a closed-loop system creating a clean energy, zero-emission (or near zero-emission) method, system, and apparatus.

Figure 3:
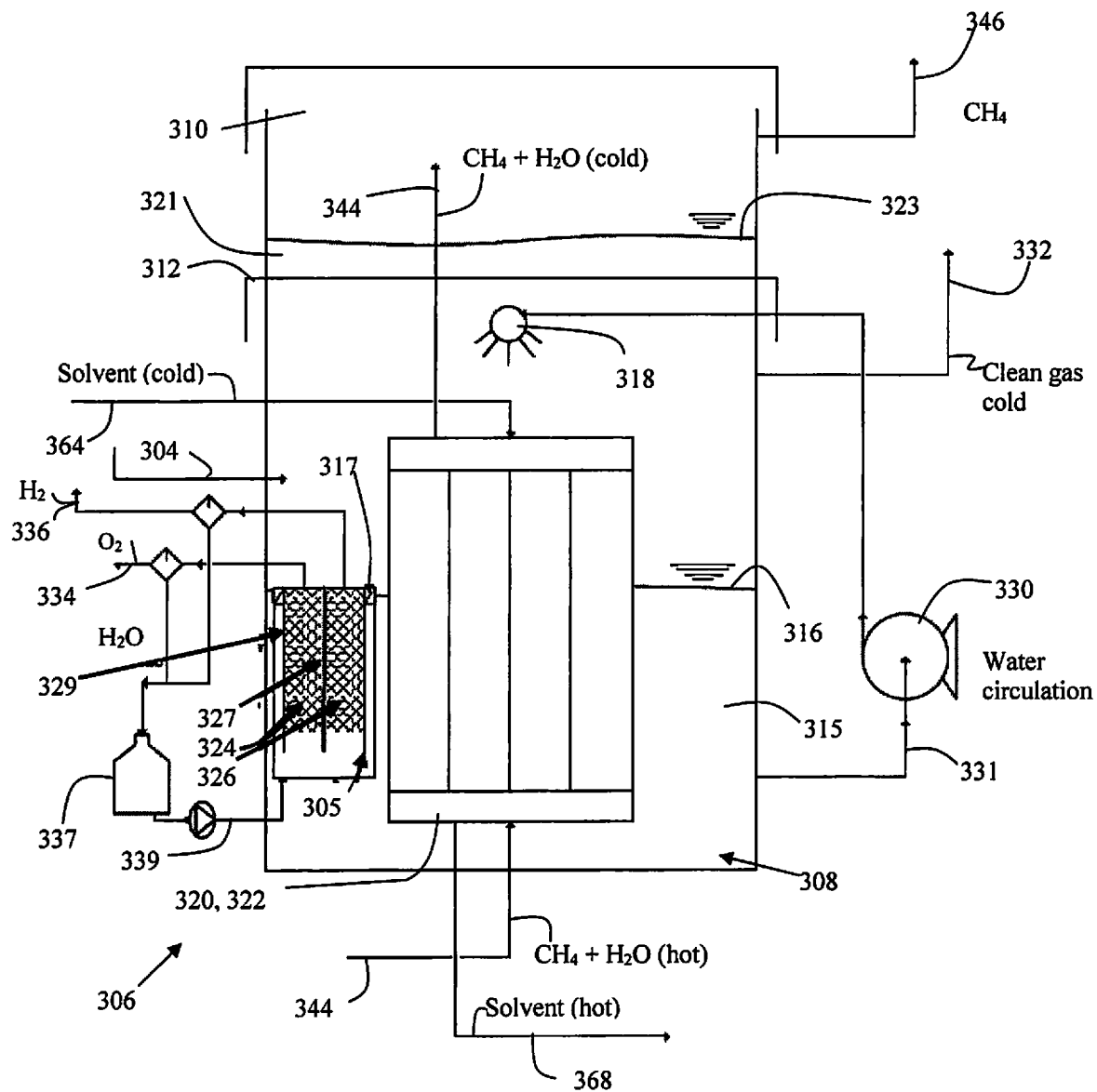
FIG. 3 is a schematic diagram of an embodiment of a SET/separator tank according to an exemplary embodiment.

An exemplary embodiment of a SET/separator tank suitable for the system (100) is generally represented in FIG. 3 by reference numeral (306). Like reference numerals are used for like parts between FIGS. 1 and 3, with the hundredths numeral "1" being changed to "3" for like parts of FIG. 3. Thus, the exhaust stream (104), SET/separator tank (106), SET chamber (108), methane separation chamber (110), partitioning wall (112), liquid (115), liquid level line (116), spray mechanism (118), first and second heat exchangers (120) and (122), condensate (121), condensate line (123), anode (124), cathode (126), pump (130), and conduits (131), (132), (134), (136), (144), (146), (164), and (168) are represented in FIG. 3 by reference numerals (304), (306), (308), (310), (312), (315), (316), (318), (320), (322), (321), (323), (324), (326), (330), (331), (332), (334), (336), (344), (346), (364), and (368), respectively. The first and second heat exchangers (120) and (122) of FIG. 1 are combined and represented by a single heat exchanger (320)/(322) in FIG. 3.

In an exemplary embodiment, an electrolysis cell (305) is positioned inside the SET chamber (308). A non-conductive separator (327) is positioned within the electrolysis cell (305) to separate the electrode chambers holding the anode (324) and the cathode (326). The electrolysis cell (305) may also be provided with a non-conductive cell or envelope (329).

In an exemplary embodiment, the liquid, e.g., water (unnumbered) of the electrolysis cell (305) is physically isolated from the remainder of the bulk fluid (315) inside the SET tank (308). The physical isolation of the liquid of the electrolysis cell (305) and the bulk fluid (315) of the SET tank (308) provides advantages of pH control and substantially isolating solid particulates inside the bulk fluid (315) of the SET chamber (308) from the electrolysis cell (305) (as discussed below in connection with filter (317)). In an embodiment, installation of multiple (not shown) electrolysis cells inside the SET chamber (308) in this manner establishes a manifold of multiple electrolysis cells such that a single high voltage power feed can be split and provide low voltage power to the individual electrolysis cells.

Excess bulk fluid (315) inside of the SET chamber (308) flows through a filter (317) into the electrolysis cell(s) as the liquid (e.g., water) is captured from the cooled combustion exhaust (304) and the methanation reaction products (334). In an embodiment, this configuration provides for optimization of the thermal mass (e.g., the water or other liquid (115)) of the SET chamber (308) versus the electrolysis cells (e.g., 305) to ensure a thermally stable environment.

The pH of the electrolysis cell (305) may become lower as a result of the dilutive bulk fluid (e.g., water) (315) added from the SET chamber (308), e.g., through the filter (317). To maintain the pH at a desirable level, according to an embodiment a separate reservoir of highly alkaline solution, such as potassium hydroxide (KOH), sodium chloride (NaCl), or one or more other electrolytes is fed to the electrolysis cell (305) as needed or desired to maintain a desirable pH. In an exemplary embodiment, pH is maintained at about 10.

According to an embodiment, the water level (316) in the SET chamber (308) is maintained via conservation of hydrogen atoms via reclamation of water from the methanation reaction products and the combustion exhaust, and makeup water added to the SET chamber (308) via a separate makeup water line as needed or desired. In an embodiment, the water level (316) in the SET chamber (308) is maintained at the level of the inlet/filter (317) to the electrolysis cell(s) (305) to ensure the electrolysis cell(s) (305) have a constant supply of fluid (e.g., water) for producing hydrogen.

Figures 4A, 4B:
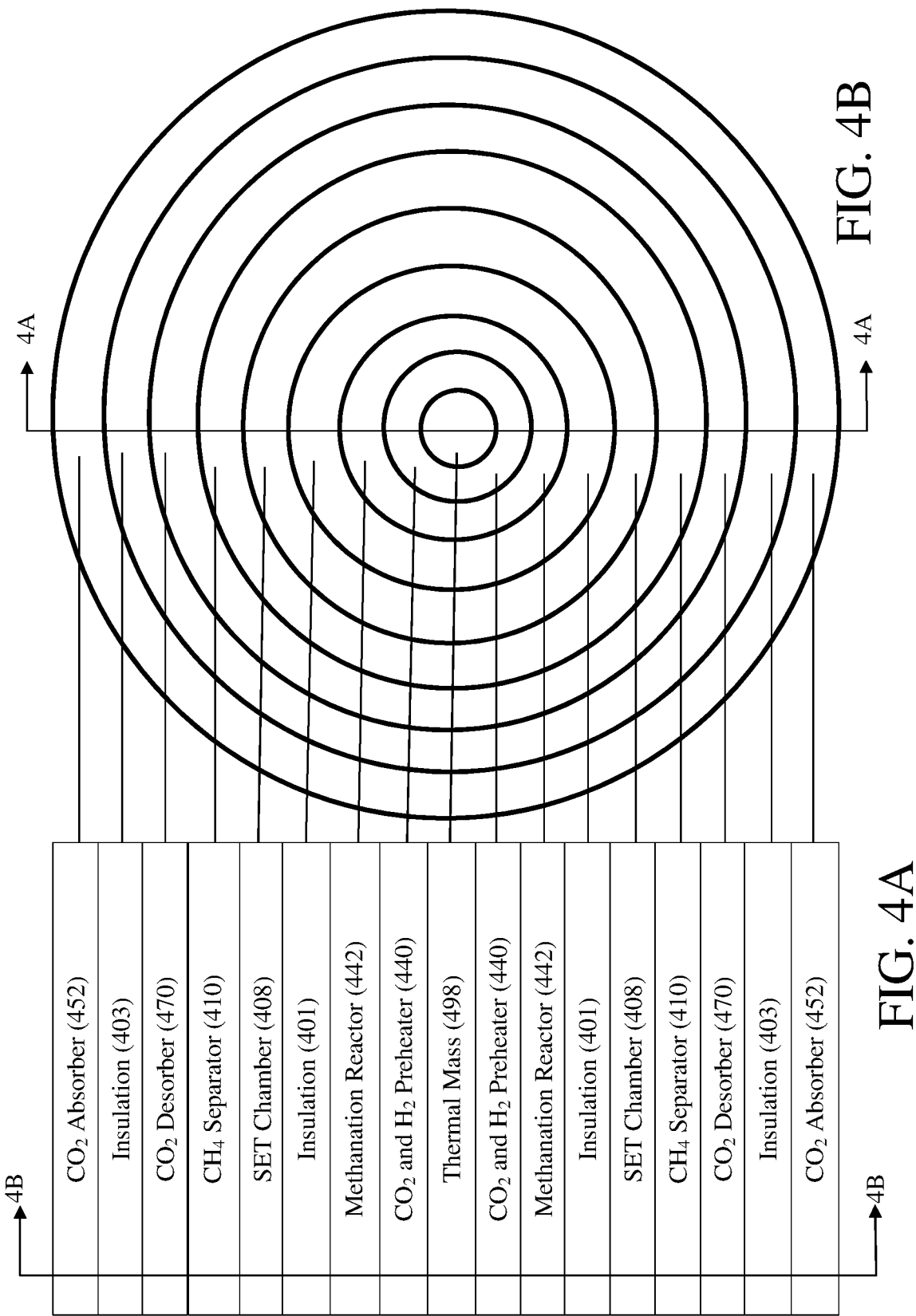
FIG. 4A is a cross sectional view taken along sectional line 4A-4A of FIG. 4B of an apparatus according to an exemplary embodiment.
FIG. 4B is a cross-sectional view taken along sectional line 4B-4B of the apparatus of FIG. 4A.

In an exemplary embodiment, the electrolysis electrodes (324) and (326) (or (124) and (126) in FIG. 1) are installed inside insulated lines, such as insulated hoses, so that the oxygen ($O_2$) and hydrogen ($H_2$) bubbles go naturally up the hoses and out of the electrolysis cell (305) via conduits (334) and (336), respectively, to their own isolated chambers (not shown). Alternatively, the oxygen and hydrogen may be recycled or used for other purposes. For example, the conduit (336) carrying the hydrogen may be directed to a methanation pre-heater or methanation reactor. In FIG. 3, the conduits (334) and (336) each include water traps (unnumbered, but shown as diamonds) that capture water in a tank (337) for recycling back into the electrolysis cell (305) via a conduit (339). An exemplary embodiment of an apparatus for carrying out the system (100) is generally represented in FIGS. 4A and 4B by reference numeral (400). Like reference numerals are used for like parts between FIGS. 1, 4A, and 4B, with the hundredths numeral "1" used in FIG. 1 being changed to "4" for like parts of FIGS. 4A and 4B. Thus, the thermal mass (198), the pre-heater (140), the methanation reactor (142), the SET chamber (108), the methane separation chamber (110), the carbon dioxide desorber (170), and the carbon dioxide absorber (152) are represented in FIGS. 4A and 4B by reference numerals (498), (440), (442), (408), (410), (470), and (452), respectively.

The apparatus (400) of FIGS. 4A and 4B comprises a plurality of chambers positioned radially outside of one another, and in an exemplary embodiment substantially concentric to one another. The thermal mass (498) is positioned at a center of the apparatus (400). The pre-heater (440) surrounds, and in an exemplary embodiment is substantially concentric to, the thermal mass (498). The methanation reactor (442) surrounds, and in an exemplary embodiment is substantially concentric to, the pre-heater (440). A first or inner insulation layer (401) is interposed between the methanation reactor (442) and the SET chamber (408), which surrounds, and in an exemplary embodiment is substantially concentric to, the first or inner insulation layer (401). The SET chamber (408) is surrounded by, and in an exemplary embodiment substantially concentric to, the methane separator (410), which is surrounded by, and in an exemplary embodiment substantially concentric to, the carbon dioxide desorber (470). A second or outer insulation layer (403) surrounds, and in an embodiment is substantially concentric to, the carbon dioxide desorber (470). The carbon dioxide absorber (452) surrounds, and in an exemplary embodiment is substantially concentric to, the second or outer insulation layer (403).

According to an embodiment, the temperatures of the chambers increase in a direction annularly inward, i.e., so that the hottest chambers are at or near the center of the apparatus (400) (e.g., the thermal mass chamber (498)) and the coolest chambers are at or near the outer periphery of the apparatus (400) (e.g., the carbon dioxide absorber chamber (452)).

The apparatus (400) of FIGS. 4A and 4B illustrates the architecture, functionality, and operation of a possible implementation of systems and methods described herein. In some alternative implementations, the arrangement of chambers in the apparatus (400) may be repositioned (e.g., transposed, switched) with respect to one another, depending upon the functionality involved. Two or more chambers shown substantially concentrically arranged may be combined and embodied as a single chamber. Alternatively, single chambers may be divided into multiple chambers, e.g., multiple concentric chambers, relative to the illustrated embodiment of the apparatus (400) of FIGS. 4A and 4B. One or more of the chambers of the apparatus (400) may be omitted. One or more additional chambers not shown in FIGS. 4A and 4B may be added to the apparatus (400). The first and second insulation layers (401) and (403), respectively, may be positioned at other locations than shown or omitted. Additionally insulation layers not shown in FIGS. 4A and 4B may be added to the apparatus (400) between any of the chambers and/or around the outside of the apparatus (400).

In an embodiment, the design of the apparatus (400) permits implementation of all or part of the system (100) and operation of all or part of the method (200) within a cylindrically constructed apparatus. The apparatus (400) may be scaled as needed or desired. According to a non-limiting embodiment, the apparatus (400) is sufficiently compact to fit through a standard 2.5 foot (0.762 m)×7 foot (2.13 m) doorway.

Figure 5:
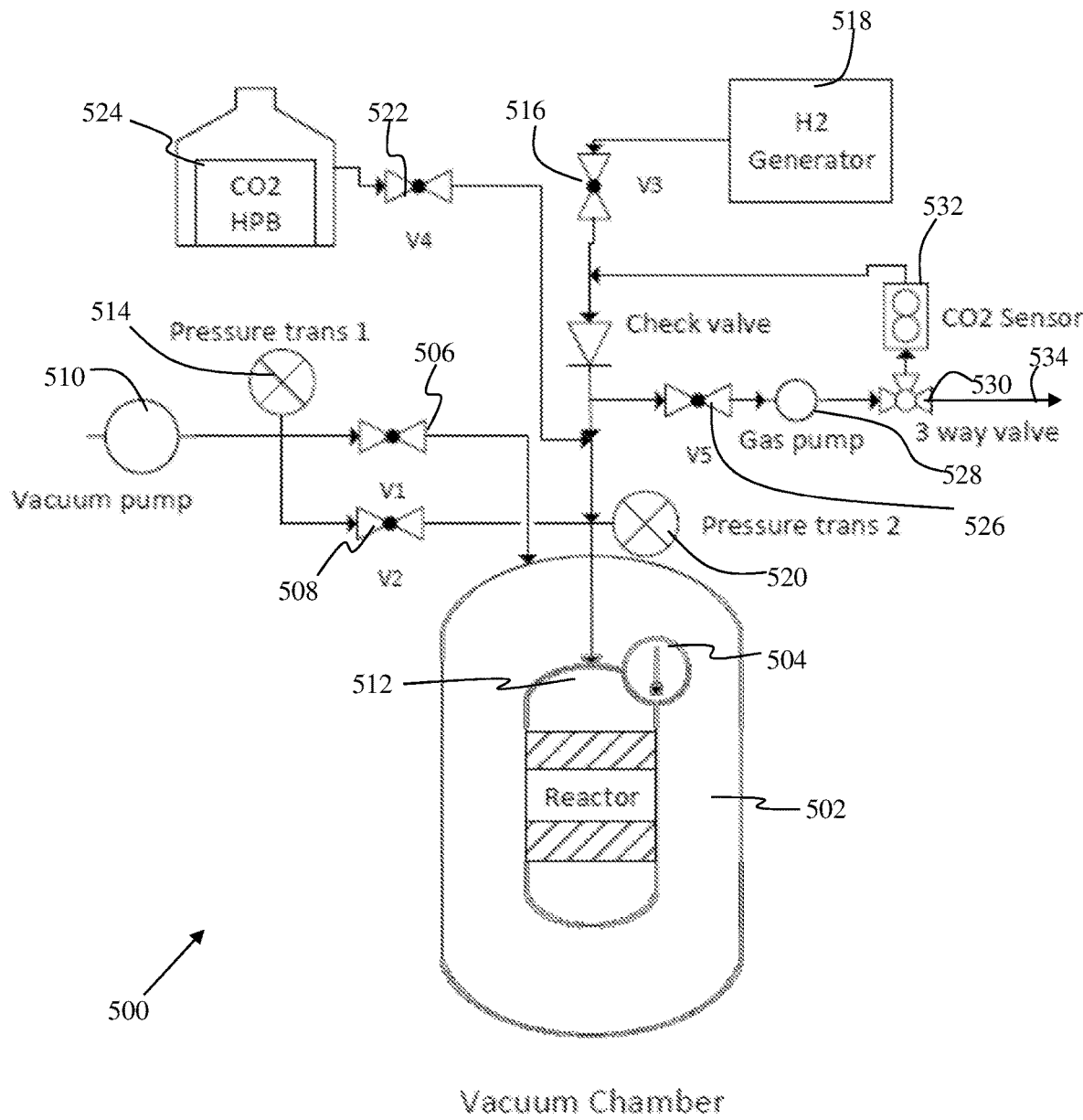
FIG. 5 is a schematic diagram of a methanation system according to an embodiment.
Figure 6:
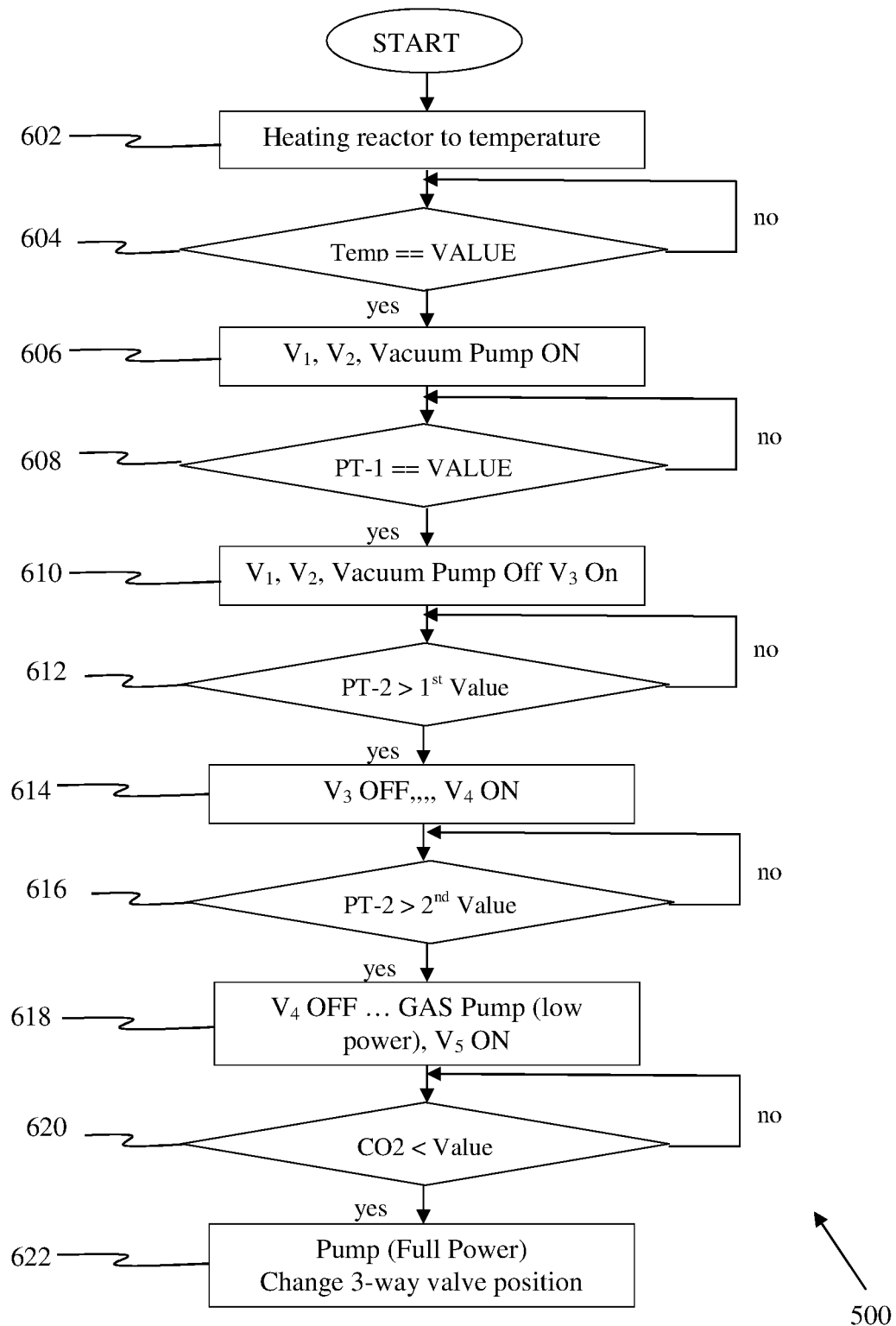
FIG. 6 is a flowchart of a method of operating the methanation system of FIG. 5.

FIG. 5 is a schematic diagram of a methanation system (500) according to an embodiment, and FIG. 6 is a flowchart (600) for operation of the methanation system (500) of FIG. 5. FIGS. 5 and 6 are applicable to the batch operation of a reactor (502), such as a Sabatier reactor. It should be understood that the following steps and operation are provided by way of example and are not limiting. For example, in alternative embodiments a Sabatier reactor may be operated in a continuous process manner.

1. The reactor (502) is heated (602) to a predetermined temperature suitable for carrying out methanation by heating the catalyst within the reactor (502). In an embodiment, heating may be carried out via an electric resistance coil. A thermocouple (504) is used for temperature measurement and collection of data. If a determination (604) is made that a predetermined temperature value has not been reached, heating continues. If a determination (604) is made that the predetermined temperature value has been reached, the process continues to step (606).

2. In step (606), ball valves $V_1$ (506) and $V_2$ (508) are turned on (i.e., opened) and a vacuum pump (510) operates to vacuum conduits connected to the vacuum pump (510) and a chamber (512) of the reactor (502). For automatic opening and closing of valves $V_1$ (506) and $V_2$ (508), low voltage solenoid relay valves operating in a range of 0 to 5 Volts may be used. In an embodiment, industrial control valves are operated at high voltage input. A determination (608) is made whether a first predetermined pressure (e.g., above 1 bar, such as 1.1 bar) as measured by a pressure transducer (trans 1) (514) has been reached inside the reactor (512). If the determination (608) is answered in the negative, the vacuum pump (510) continues to operate.

3. When the determination (608) is made that the pressure transducer (trans 1) (514) has achieved the predetermined pressure, the vacuum pump (510) stops, and the ball valves $V_1$ (506) and $V_2$ (508) are turned off (i.e., closed), and ball valve $V_3$ (516) is turned on (610) (i.e., opened). According to an embodiment, predetermined pressure valves (e.g., 1 Pascal or 10 Pascal) may be used for any or all valves, e.g., (506), (508), (516), (522), and/or (526). Although ball valves are shown and described herein, it should be understood that other types of valves may be used.

4. After the valve $V_3$ (516) is turned on (i.e., opened) (610), and the reactor (502) fills with hydrogen supplied by hydrogen generator (518) until a determination (612) is made that the pressure transducer (trans 2) (520) has achieved, e.g., exceeds, a predetermined pressure value, according to mass stoichiometry.

5. In step (614), the valve $V_3$ (516) is turned off (i.e., closed) and valve $V_4$ (522) is turned on (i.e., opened). The reactor (502) fills with carbon dioxide from carbon dioxide source (524) until a determination (616) is made that the Pressure Trans 2 (520) achieves a predetermined pressure value, according to mass stoichiometry.

6. The valve $V_4$ (522) is turned off (i.e., closed) (618), so that at this point, all of the valves $V_1$ (506), $V_2$ (508), $V_3$ (516), and $V_4$ (522) are off. Valve $V_5$ (526) is turned on (i.e., opened) (618). A gas pump (526) circulates samples from the reactor (502) and the carbon dioxide percentage is measured by a carbon dioxide sensor (532).

7. When a determination (620) is made that a predetermined carbon dioxide percentage value (as measured by the $CO_2$ sensor (532)) is achieved, a three-way valve (530) is opened and the gas pump (528) aspirates the gas mixture (622) from the reactor (502) by adjusting the position of the three-way valve (530) such that the gas mixture may leave the reactor (502) and the connected piping (534). After this step, the reactor (502) is ready for another batch operation, at which point the three-way valve (530) is adjusted to prevent the gas mixture from leaving the piping (534) connected to the reactor (502) and instead causes the gas mixture to circulate between the reactor (502) and the CO2 sensor (532).

An Electrolysis Controller Equation: In an embodiment, a decision whether or not to run the electrolysis system and produce hydrogen in the SET chamber/tank is driven by balancing the price of electricity, the price of natural gas, and the pressure of the methanation reactor, that is, if the methanation reactor and its associated preheater are depressurized such that the reactor and preheater are capable of receiving hydrogen that is produced.

In an exemplary embodiment, the incorporation of the electrolysis system within the SET tank creates a thermally stable environment for the rapid on/off operational cycle of the electrolysis system, where heat transfer within the SET tank (e.g., from the methanation products to the saturated solvent and liquid (e.g., water) in the SET tank (108)) is regulated based on whether the electrolysis system is activated. Regulation may include controlling the flow rate of the saturated solvent stream (164), e.g., slower solvent flow rates increase heat transfer. The specified Electrolysis Controller Equation is implemented in an embodiment described herein as a result of the SET tank/chamber environment for the electrolysis system and the batch operational mode of the methanation reactor. In an embodiment, the Electrolysis Controller Equation prescribes rapid on/off cycles. The batch methanation reactor accommodates the sporadic nature, if any, of the hydrogen production and the SET tank accommodates any sporadic heat output of the electrolysis system.

In an embodiment, rapid venting of the hydrogen into the methanation pre-heater (140) prevents a buildup of products around the electrodes, which would impede the hydrolysis reaction. This is expressed mathematically as follows:

E1=ON=>Electrolysis is active and producing hydrogen/oxygen inside the SET tank, If (the total value of methane produced>the total value of electricity purchase AND the pressure sensor on the H2 generator outlet, S2<1 bar=>, THEN active depressurization of the methanation reactor to prepare for receipt of hydrogen and carbon dioxide).

E1=OFF=>Electrolysis is inactive and not producing hydrogen and oxygen inside the SET tank.

Natural Gas Valuation: In an embodiment, the total value of methane produced is variable based on the market conditions for both electricity purchased and methane sold. For example, if the user selects on the system control for natural gas to be sold on the open market, and the user is able to sell natural gas into a renewable natural gas market, then the system control will reach the daily renewable natural gas price and that will be the value of the natural gas produced. In an embodiment, natural gas produced by the system is only certified as "renewable" if the electricity used for electrolysis derives from a renewable source, such as solar panels, wind turbines, etc. In an embodiment, if the electrolysis system is connected directly to a source of renewable electricity, then the natural gas produced will be rated as renewable. On the other hand, if the electrolysis system is connected to the grid, then the electrolysis system will treat the electricity inputted as from a mixed source proportional to the electricity on the grid at the time of operation per the specifications of the grid operator. The above implementations relating to natural gas valuation are provided by way of example only, and are not limiting.

Figure 7:
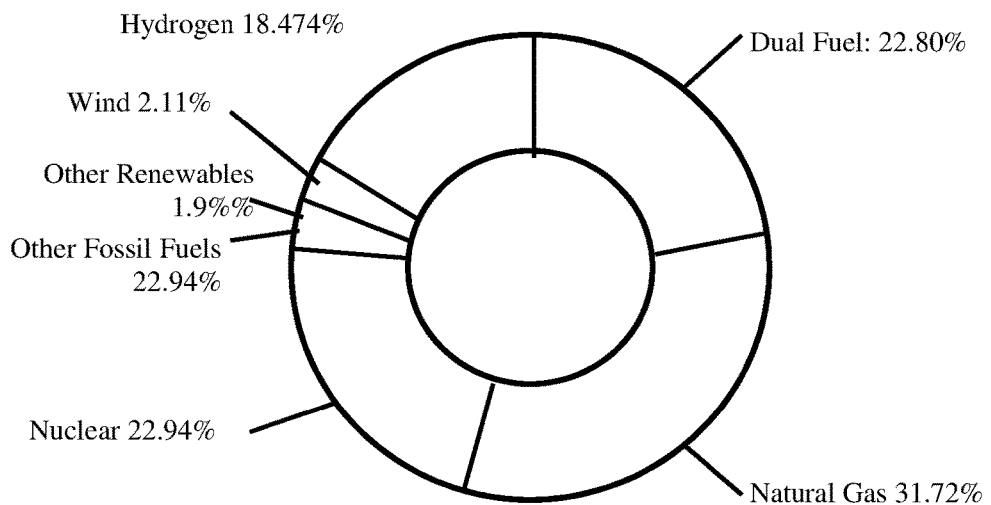
FIG. 7 is an illustrative example of a makeup of electricity generator sources for providing energy to a given geographical error (e.g., New York State) at a given day and time.

For example, FIG. 7 shows the readout of an electrolysis system operating in NYS at the time shown. The embodiment illustrated in FIG. 7 depicts a makeup of electricity generator sources at a specific time. For example, electricity consumed at the time captured by FIG. 7 is about 23% nuclear derived.

Only about 21% (i.e., 2% wind, 18% hydro, and 1% other renewable) of the electrolysis system of FIG. 7 is considered as being fed from a renewable source and thus 21% of the natural gas produced would be rated as renewable, and the remainder of the produced natural gas would be rated as non-renewable.

The value of the natural gas produced would in turn be the blended price of the renewable natural gas and non-renewable natural gas prices, assuming the natural gas is set to be sold on the market accordingly. In an embodiment, in the event the natural gas is contracted to be sold at a fixed price then that valuation is applied.

In an embodiment, in the event that the natural gas produced is set to a net meter where the facility operates the existing natural gas meter in reverse and provides a credit, then the valuation of the natural gas is set to be the all-in supply+delivery+taxes cost of the natural gas previously purchased at the facility on the condition that natural gas was previously purchased within the appropriate billing period to avoid charges. If there was no natural gas previously consumed within the billing period then the natural gas would be valued at whatever price the natural gas utility charges for gas fed to the grid.

Electricity Valuation: In an embodiment, the value of the electricity supplied to the electrolysis process is either a fixed cost applied to the system controller connected to the grid or the value is a function of the rates, tariffs and locational based pricing for the 5 minute interval of pricing applied at the time of consuming electricity. For example, if the electricity is to be purchased in NYS Zone J is $44.17/MWh, then the commodity price of the electricity prior to adding any additional utility based charges would be $44.17/MWh and this value would change every 5 minutes.

In an embodiment, the electrolysis controller (125) is designed to interface with all natural gas markets and utilities to account for all of the above scenarios when providing a valuation of the natural gas that is produced.

SET Tank Controller Equation: In exemplary embodiments, the SET tank is maintained at 80° C.

In embodiments, there may be one or more sources for heating the SET tank. In an embodiment, the only source of cooling the SET tank is the solvent pump (166) that feeds rich cold solvent via a heat exchanger through the SET tank in order for the solvent to be heated and the liquid (e.g., water) in the SET tank to be cooled. The tandem pump to pump P1 (166) is the pump P2 (184), which takes hot lean solvent from the desorber. In an embodiment, the speed and size of the pump P2 (184) is maintained equal to the speed and size of the pump P1 (166) in order to maintain a mass balance on the solvent in the system.

In an embodiment, the size of the pump P1 (166) is set such that it may normally operate at a relatively low speed of 30% of its capacity but when operating at 100% of its capacity has the ability to provide cooling capacity that can match the heat output of the SET tank when all sources of heat in the SET tank (e.g., electrolysis, combustion exhaust (104), and methanation reactor outlet (144)) are at their maximum potential.

In an embodiment, the operation of the pump P1 (166) is also influenced by the carbon dioxide percent at the outlet of the absorber (152). For example, in an embodiment the speed of the pump P1 (166) is increased in order to ensure the carbon dioxide percent at a CO2 sensor (not shown in FIG. 1) installed on the $N_2$ exhaust conduit (162) is equal to zero.

Thus the mathematical description of the control of the pump P1 (166) according to an embodiment is as follows, where the CO2 sensor "S1" is installed on conduit (162) in FIG. 1:

Speed of the pump P1=f(SET-tank temperature, S1-CO2%)

wherein in an embodiment the pump P1 increases/decreases its speed in order to maintain:

SET tank temperature <81 C
S1 CO2%=0

The Tables 1 and 2 below set forth non-limiting examples of assumptions based on calculations system performance for hypothetical technical specifications and system interconnections according to an embodiment.

| Technical Specifications | | | |
|---|---|---|---|
| | Generator Rated Electrical Output | | |
| | 250 kW | 500 kW | 1 MW |
| System Dimensions | 3.01 × 2.35 × 2.36 m (16 m³) | 5.89 × 2.35 × 2.36 m (33 m³) | 12.03 × 2.4 × 2.36 m (67.7 m³) |

| Technical Specifications -continued | | | |
|---|---|---|---|
| | Generator Rated Electrical Output | | |
| | 250 kW | 500 kW | 1 MW |
| CO₂ Capture Rate [Tonnes/Year] | 500 | 1,000 | 2,000 |
| Peak Electric Power Input [MW] | 3.5 | 7 | 14 |
| Continuous Electric Power Input [kW] | 50 | 100 | 200 |
| Synthetic Natural Gas Output [MMBtu/Year] | 9,338 | 18,767 | 37,352 |
| Renewable Electricity Consumption [MWh/Year] | 4,329 | 8,658 | 17,316 |
| Net System Efficiency (Lower Heating Value Basis) | 64% | 64% | 64% |
| Synthetic Natural Gas Storage Capacity [MMBtu] | 179.96 | 359.91 | 719.82 |

TABLE 2

| System Interconnections | | | |
|---|---|---|---|
| Electrical Connection Option A | AC 460 V \| 3 PH 25,000 Amps | AC 460 \| 3 PH 50,000 Amps | AC 460 \| 3PH 100,000 Amps |
| Electrical Connection Option B | AC 460 V \| 3 PH 5,000 Amps + 10 MW DC Input | AC 460 V \| 3 PH 5,000 Amps + 20 MW DC Input | AC 460 V \| 3 PH 5,000 Amps + 40 MW DC Input |
| Tap Water Connection | 0.5 inch | 0.5 inch | 0.5 inch |
| Sewer Water Connection | 1 inch | 1 inch | 1 inch |

Embodiments described above utilize a Sabatier reactor and process in a scalable manner so that various sources of carbon dioxide (e.g., combustion appliance (102)) may be retrofitted with equipment embodied herein in order to use intermittent renewable electricity to convert carbon dioxide and water emissions into methane. A result is an embodiment in which an existing fossil-fuel fired combustion appliance may be turned into a 100% carbon neutral system that maintains a closed loop on carbon.

In an exemplary embodiment, all or substantially all of the hydrogen generated during electrolysis is fed to the methanation reactor, in which a catalytic reaction may proceed at high temperature, e.g., about 350° C. In an exemplary embodiment, all or substantially all of the hydrogen is burned in the methanation reaction substantially immediately or instantaneously after the hydrogen has been generated. In exemplary embodiments, the purity of the hydrogen does not need to be very high, which contrasts embodiments described herein against commercial processes requiring hydrogen purity of 99% or greater. In an embodiment, gases present with the hydrogen are burned as well. Thus, the gas flow into the methanation reactor may be well below 99% purity, for example, on the order of about 70 mass percent hydrogen and 30 mass percent other gases. In exemplary embodiments, the ability to process hydrogen streams having relatively low purities provides greater design flexibility that other hydrogen generator manufacturing systems lack.

In exemplary embodiments, energy efficiency considerations may similarly differ from those generally practiced in commercial processes. While high efficiency is desirable, embodiments described herein may be practiced at lower electrolysis efficiencies of, for example, about 50% while still operating the overall system at a high efficiency. In the commercial market, the incremental manufacturing costs to achieve pure hydrogen and high electrolysis efficiencies are extremely large. It is the difference between using lesser expensive equipment (e.g., commodity stainless steel components) versus more expensive equipment (e.g., expensive platinum catalysts and/or rare earth elements etc.). Accordingly, embodiments described herein provide for capital cost savings by allowing for the use of lesser expensive equipment because high purity hydrogen generation is not required.

Embodiments disclosed herein are directed to systems, apparatuses, and methods configured to achieve, in particularly exemplary embodiments, at least one of the following objects and advantages. First, combustion emissions, such as from a hydrocarbon combustion appliance or system, are isolated, reclaimed, and reused. In an exemplary embodiment, carbon dioxide isolated from the combustion emissions and hydrogen generated from water of the combustion emissions are converted into hydrocarbons, such as methane via methanation. Second, heat generated by methanation can be utilized in other parts of the process, apparatus, and system, such as in the SET tank to drive the electrolysis and/or heat the solvent containing captured carbon dioxide delivered from the carbon dioxide absorber before the solvent is forwarded to the carbon dioxide desorber. Third, water from the combustion emissions can be separated and electrolyzed in an efficient manner for the purpose of generating hydrogen for the methanation reaction. Fourth, the methane can be recycled back into a power plant or other system for further use and/or can be put to other uses.

It should be understood that the process is scalable, including, for example and not by limitation, from a 5 kW residential backup generator to a 500 MW or greater capacity power plant.

In a particularly advantageous embodiment, the method and system may be integrated with one or more natural energy sources, such as photovoltaic solar cells, to operate equipment of the system and carry out steps of the method. For example, photovoltaic energy may be used to power the electrolysis, the dry cooler, the compressor for methane compression, pumps, fans, control systems, peripheral loads, or any combination thereof. In an exemplary embodiment, the method and system are practiced without the use of fossil fuels.

Certain embodiments disclosed herein efficiently integrate thermal separation of water and chemical capture/absorption of carbon dioxide to separate carbon dioxide from other constituents of an exhaust stream, including but not limited to water and nitrogen.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any claim unless recited in the claim.

As used herein, the terms "comprises," "comprising," "includes," "including," "has," "having" or any other variation thereof, are intended to cover a non-exclusive inclusion. For example, a process, method, system, or apparatus that comprises a list of features is not necessarily limited only to those features but may include other features not expressly listed or inherent to such process, method, system, or apparatus. Also, the use of "a" or "an" are employed to describe elements and components described herein. This is done merely for convenience and to give a general sense of the scope of the disclosure. This description should be read to include one or at least one and the singular also includes the plural unless it is obvious that it is meant otherwise. If a specific number of an introduced claim element is intended, such intent will be explicitly recited in the claim, and in the absence of such recitation no such limitation is present. For a non-limiting example, as an aid to understanding, to the extent that the following appended claims contain usage of the introductory phrases "at least one" and "one or more" to introduce claim element, the use of such phrases should not be construed to imply that the introduction of a claim element by the indefinite articles "a" or "an" limits any particular claim containing such introduced indefinite article and claim element to embodiments containing only one such element, even when the same claim includes the introductory phrases "one or more" or "at least one" and indefinite articles such as "a" or "an"; the same holds true for the use in the claims of definite articles.

The various components and features of the above-described exemplary embodiments may be substituted into one another in any combination. It is within the scope of the invention to make modifications necessary or desirable to incorporate one or more components and features of any one embodiment into any other embodiment. One skilled in the art, using the disclosures provided herein, will appreciate that various steps of the methods can be omitted, rearranged, combined, supplemented with additional steps, and/or adapted in various ways. For example, in one or more embodiments an alternative carbon dioxide capture and release technique may be employed, such as but not limited to physical adsorption."

The foregoing description of the exemplary embodiments and exemplary methods has been provided for the purpose of explaining principles of the invention and its practical application, thereby enabling others skilled in the art to understand the invention for various embodiments and with various modifications as are suited to the particular use contemplated. The description is not necessarily intended to be exhaustive or to limit the invention to the precise embodiments disclosed.

The flowchart and block diagrams in the Figures illustrate the architecture, functionality, and operation of possible implementations of systems, apparatuses, and methods according to various embodiments of the present embodiments. In some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved.

It will be appreciated that, although specific embodiments have been described herein for purposes of illustration, various modifications may be made without departing from the spirit and scope of the embodiments. Accordingly, the scope of protection of the embodiments is limited only by the following claims and their equivalents.

What is claimed is:
1. A method comprising:
receiving a hydrocarbon combustion exhaust stream comprising water and carbon dioxide in a first chamber containing liquid water;

conveying methanation reaction products through a first heat exchanger of the first chamber to transfer heat from the methanation reaction products to the liquid water; and subjecting the heated liquid water to electrolysis in the first chamber to generate hydrogen and oxygen.

2. The method of claim 1, further comprising:
capturing the carbon dioxide in a solvent;
heating the solvent and the captured carbon dioxide in a second heat exchanger of the first chamber, wherein the first and second heat exchangers comprise a common heat exchanger or different heat exchangers; and
separating at least a portion of the carbon dioxide from the heated solvent.

3. The method of claim 2, wherein the capturing of the carbon dioxide in a solvent takes place in a carbon dioxide absorber, and wherein the separating at least a portion of the carbon dioxide from the heated solvent takes place in a carbon dioxide desorber.

4. The method of claim 3, further comprising:
discharging a first stream comprising carbon dioxide and a different second stream comprising heated solvent from the carbon dioxide desorber; and
cooling the first and second streams in the carbon dioxide absorber.

5. The method of claim 3, wherein the carbon dioxide absorber is positioned substantially concentrically outside of the carbon dioxide desorber.

6. The method of claim 2, further comprising reacting at least the hydrogen generated by the electrolysis and the carbon dioxide separated from the heated solvent in a methanation reactor to generate the methanation reaction products.

7. The method of claim 6, further comprising:
heating a thermal mass with heat generated by the reacting of at least the hydrogen and the carbon dioxide in the methanation reactor; and
preheating the hydrogen generated by the electrolysis and the carbon dioxide separated from the heated solvent in a methanation pre-heater heated with the thermal mass prior to conveying the hydrogen and the carbon dioxide to the methanation reactor.

8. The method of claim 7, wherein the methanation pre-heater is positioned substantially concentrically within the methanation reactor.

9. The method of claim 7, further comprising:
the capturing of the carbon dioxide in a solvent takes place in a carbon dioxide absorber; and
the separating at least a portion of the carbon dioxide from the heated solvent takes place in a desorber.

10. The method of claim 9, wherein:
the methanation reactor is positioned substantially concentrically outside of the methanation pre-heater;
the first chamber is positioned substantially concentrically outside of the methanation pre-heater;
the carbon dioxide desorber is positioned substantially concentrically outside of the first chamber; and
the carbon dioxide absorber is positioned substantially concentrically outside of the carbon dioxide desorber.

11. The method of claim 1, further comprising separating methane from the water of the methanation reaction products in a second chamber that is different than the first chamber.

12. The method of claim 11, wherein the first chamber and the second chamber are contained in a common tank.

13. The method of claim 12, wherein the second chamber is positioned substantially concentrically outside of the first chamber.

14. The method of claim 1, wherein the hydrocarbon combustion exhaust stream comprises gaseous water, and wherein the method further comprises condensing at least a portion of the gaseous water in the first chamber to add to the liquid water in the first chamber.

15. A method comprising:
subjecting liquid water in a first chamber to electrolysis to generate hydrogen and oxygen;
capturing carbon dioxide in a solvent;
conveying the solvent and the captured carbon dioxide through a first heat exchanger of the first chamber; and
conveying methanation reaction products through a second heat exchanger of the first chamber to transfer heat from the methanation reaction products to the liquid water in the first chamber and to the solvent conveyed through the first heat exchanger of the first chamber, wherein the first and second heat exchangers comprise a common heat exchanger or different heat exchangers.

16. The method of claim 15, further comprising separating at least a portion of the carbon dioxide from the heated solvent, wherein the capturing is conducted in a carbon dioxide absorber and the separating is conducted in a carbon dioxide desorber.

17. The method of claim 16, wherein the carbon dioxide desorber is positioned substantially concentrically outside of the first chamber, and the carbon dioxide absorber is positioned substantially concentrically outside of the carbon dioxide desorber.

18. The method of claim 15, further comprising separating methane from water of the methanation reaction products in a second chamber that is different than the first chamber.

19. The method of claim 18, wherein the second chamber is positioned substantially concentrically outside of the first chamber.

20. A method comprising:
receiving a hydrocarbon combustion exhaust stream comprising water and carbon dioxide in a chamber containing liquid water;
passing methanation reaction products through a first heat exchanger of the chamber to transfer heat from the methanation reaction products to the liquid water, the methanation reaction products comprising methane and gaseous water;
subjecting the heated liquid water to electrolysis in the chamber to generate hydrogen and oxygen;
capturing the carbon dioxide in a solvent;
heating the solvent with the captured carbon dioxide in a second heat exchanger of the chamber, wherein the first and second heat exchangers comprise a common heat exchanger or different heat exchangers;
separating at least a portion of the carbon dioxide from the heated solvent; and
reacting at least the hydrogen generated by the electrolysis and the carbon dioxide separated from the heated solvent in a methanation reactor to generate one or more hydrocarbons.

* * * * *